United States Patent
Rhodes et al.

(10) Patent No.: US 10,668,176 B2
(45) Date of Patent: Jun. 2, 2020

(54) STERILIZATION TRAY

(71) Applicant: ASP Global Manufacturing GmbH, Schaffhausen (CH)

(72) Inventors: Samuel J. Rhodes, Los Angeles, CA (US); Masood Siddiqui, Irvine, CA (US); Darius D. Eghbal, Sierra Madre, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 59 days.

(21) Appl. No.: 15/828,654

(22) Filed: Dec. 1, 2017

(65) Prior Publication Data

US 2019/0167824 A1   Jun. 6, 2019

(51) Int. Cl.
| | | |
|---|---|---|
| *A61B 50/33* | (2016.01) | |
| *A61L 2/06* | (2006.01) | |
| *A61B 1/00* | (2006.01) | |
| *A61L 2/18* | (2006.01) | |
| *A61B 50/00* | (2016.01) | |
| *A61B 90/70* | (2016.01) | |
| *A61B 50/20* | (2016.01) | |
| *A61L 2/26* | (2006.01) | |

(52) U.S. Cl.
CPC ............ *A61L 2/06* (2013.01); *A61B 1/00144* (2013.01); *A61B 50/00* (2016.02); *A61B 50/20* (2016.02); *A61B 50/33* (2016.02); *A61B 90/70* (2016.02); *A61L 2/18* (2013.01); *A61L 2/26* (2013.01); *A61B 2050/005* (2016.02); *A61B 2050/007* (2016.02); *A61B 2090/701* (2016.02); *A61L 2202/10* (2013.01); *A61L 2202/24* (2013.01)

(58) Field of Classification Search
CPC ..... A61L 2/06; A61L 2/18; A61L 2/26; A61L 1/00144; A61L 2202/10; A61L 2202/24; A61B 50/00; A61B 50/20; A61B 50/33; A61B 90/70; A61B 2050/005; A61B 2050/007; A61B 2090/701
See application file for complete search history.

(56) References Cited

U.S. PATENT DOCUMENTS

| | | | |
|---|---|---|---|
| 5,759,490 A * | 6/1998 | Malchesky | A61L 2/04 285/422 |
| 6,099,812 A | 8/2000 | Allen et al. | |
| 6,193,932 B1 | 2/2001 | Wu et al. | |
| 6,264,902 B1 * | 7/2001 | Howlett | A61L 2/26 422/300 |
| 6,379,631 B1 | 4/2002 | Wu | |
| 6,572,819 B1 | 6/2003 | Wu et al. | |
| 6,692,693 B2 | 2/2004 | Wu | |
| 7,993,602 B2 * | 8/2011 | Moriyama | A61B 1/123 400/300 |
| 2002/0191938 A1 | 12/2002 | Sheetz et al. | |

* cited by examiner

*Primary Examiner* — Timothy C Cleveland
(74) *Attorney, Agent, or Firm* — Etan S. Chatlynne; Roberts Calderon Safran & Cole P.C.

(57) ABSTRACT

A sterilization tray is disclosed herein. A medical instrument, such as an endoscope, may be placed into the sterilization tray, and the sterilization tray with the medical instrument disposed therein may be placed into a vacuum chamber of a sterilization system. The sterilization tray may also be used to transport the medical instrument to and from a point of care. Sterilization is performed with the instrument in the base component and the lid component disposed atop the base component. Transportation is performed with the instrument in the lid component and the base component disposed atop the lid component.

11 Claims, 4 Drawing Sheets

STERILIZATION TRAY

FIELD

The subject matter disclosed herein relates to containers used for sterilizing medical instruments.

BACKGROUND

Endoscopes are reusable medical devices. An endoscope should be reprocessed, i.e., decontaminated, between medical procedures in which it is used to avoid causing infection or illness in a subject. The initial steps of reprocessing should be conducted immediately or shortly after the endoscope has been used in a procedure, at the point of care, to remove bioburden from an endoscope before it can dry on the endoscope. The initial steps are typically performed by a nurse and include, among others, wiping down the endoscope, soaking it in a detergent solution, suctioning detergent through the endoscope, suctioning air through the endoscope, and flushing the channels. After the initial steps are performed the endoscope may be transported to a reprocessing area for further reprocessing, such as disinfection or sterilization.

When the contaminated endoscope will be subject to a sterilization procedure, the endoscope may be placed into a sterilization tray, as is typical of sterilization procedures for medical devices. Following sterilization, the endo scope may be used in another procedure. The endoscope may be transported back to a procedure room (e.g., an operating room) in the tray in which it was sterilized or in another receptacle.

SUMMARY

A sterilization tray is disclosed herein. A medical instrument, such as an endoscope, may be placed into the sterilization tray, and the sterilization tray with the medical instrument disposed therein may be placed into a vacuum chamber of a sterilization system. The sterilization tray may also be used to transport the medical instrument to and from a point of care. The sterilization tray may include a base component having a first top wall, a first side wall and a first bottom wall. Two brackets may be disposed upon the first wall. The brackets may be utilized to maintain an endoscope's tubes in a coiled configuration. A lid component having a second top wall, a second side wall, and a second bottom wall, may be disposed atop the base component to cover the base component. The lid component may be taller than the base component. That is, a first distance measured from the first top wall to the first bottom wall is less than a second distance measured from the second top wall to the second bottom wall. The second distance may be between approximately 1.5 times and ten times longer than the first distance. The second distance is approximately three times longer than the first distance.

At least one hole (i.e., a first hole) may be disposed through the lid component, for example, through the first sidewall. At least one hole (i.e., a second hole) may be disposed through the base component, for example, through the second side wall. An insert configured to maintain a body of an endoscope may be disposed within the sterilization tray. The insert may include a securing mechanism, such as an elastomeric band.

The sterilization tray may be provided. An endoscope may be placed into the lid component. The lid may be covered with the base component. The base component may be removed from the lid component. The base component may be flipped. The endoscope may be removed from the lid component. The lid component may be flipped. The endoscope may be placed into the base component. The base component may be covered with the lid component. The sterilization tray with the endoscope disposed therein may be placed into a vacuum chamber of a sterilization system. The endoscope may be sterilized.

The tray may be transported from a reprocessing area to a procedure room with the endoscope disposed within the base component and with the lid component covering the base component. The tray may be transported from the procedure room to the reprocessing area with the endoscope disposed within the lid component and with the base component covering the lid component. The endoscope may be position in the base component in a coiled configuration by securing the endoscope's tubes using the brackets.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Endoscopes may be rather long, e.g., from approximately six to twelve feet, making them cumbersome to manage, particularly during the initial reprocessing steps at the point of care, e.g., a procedure room such as an operating room, and during transportation from the point of care to a reprocessing area. Thus, a need exists for facilitating such management of endoscopes, particularly endoscopes that are over six feet long.

Figure 1:
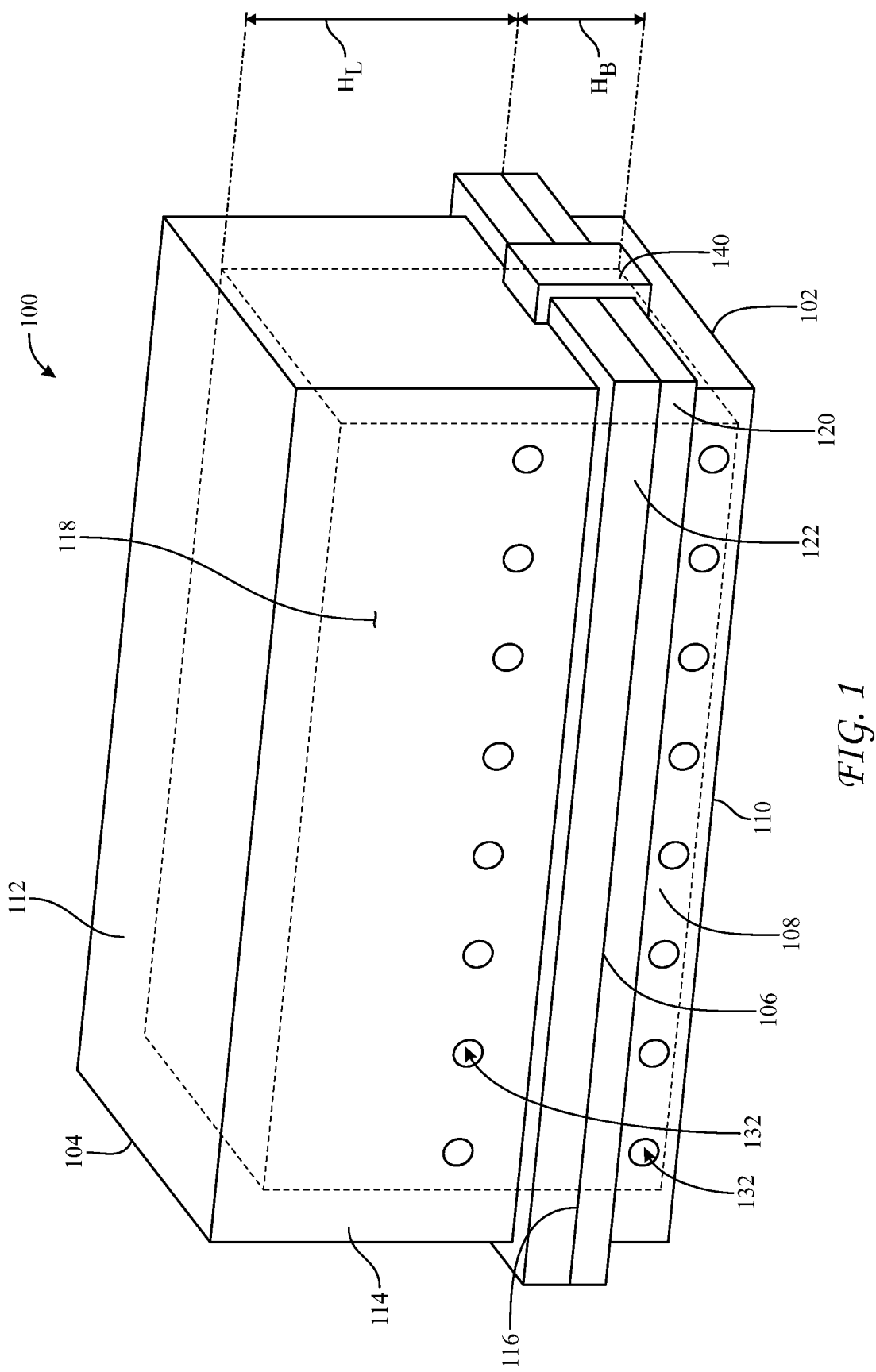
FIG. 1 depicts a perspective view of a sterilization tray.
Figure 2:
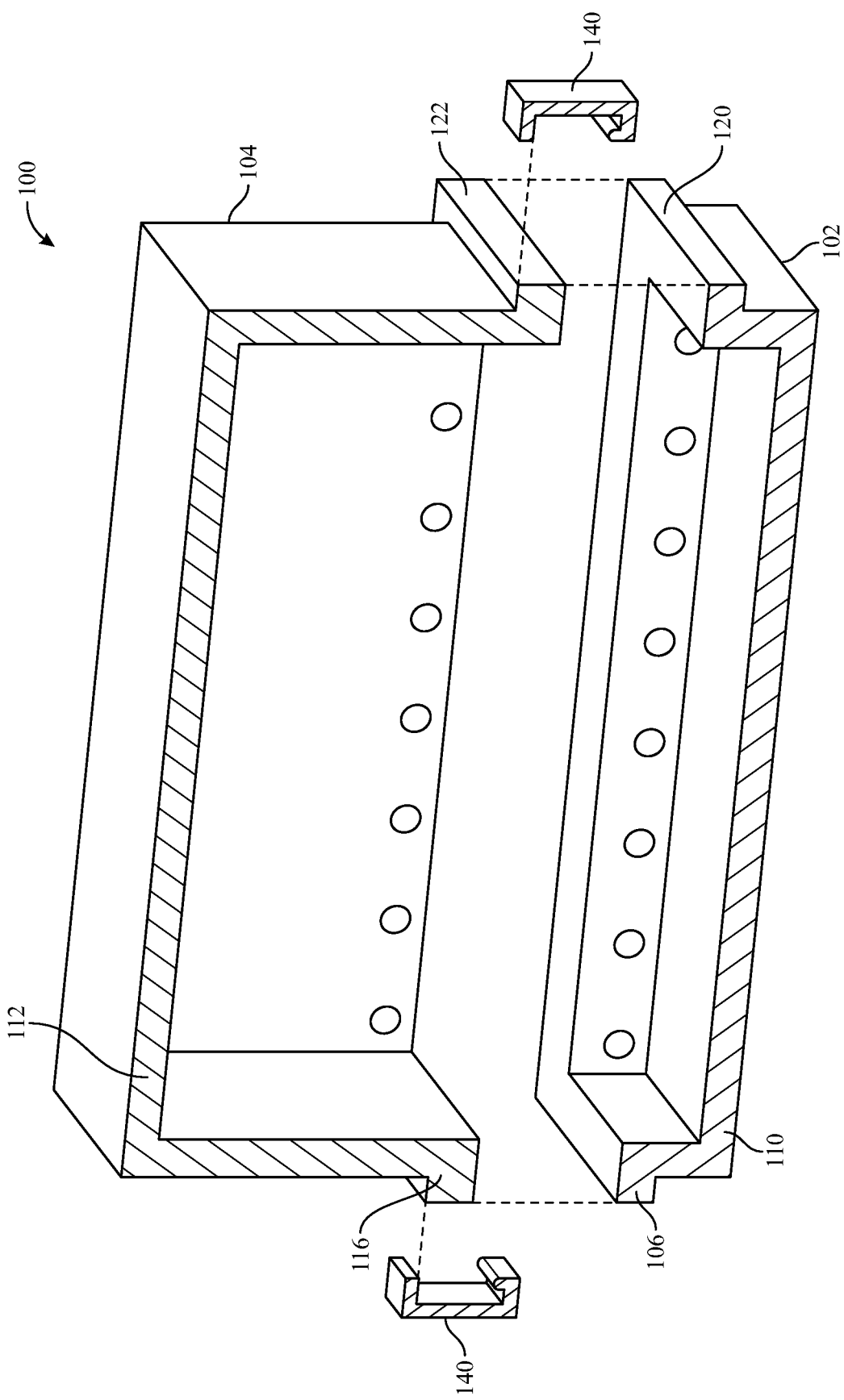
FIG. 2 depicts an exploded cross section view of the sterilization tray of FIG. 1.

FIGS. 1 and 2 show a sterilization tray 100 that includes a base component 102 and a lid component 104. Base component 102 may include a first top wall 106, a first side wall 108, and a first bottom wall 110. Lid component 104 may include a second top wall 112, a second side wall 114, and a second bottom wall 116. Lid component 104 may be disposed atop base component 102 such that it covers base component 104 to define an internal volume 118 bound by, e.g., walls 108, 110, 112, and 114. Holes 132 may be disposed through first side wall 108 and/or second side wall 114, providing a fluid connectivity from outside tray 100 through base component 102 and/or lid component 104, to internal volume 118.

Base component 102 may include a first lip 120 and lid component 104 may include a second lip 122. Lips 120 and 122 may mate to each other when lid component 104 is disposed atop base component 102. Thus, lips 120 and 122 may form a handle that a user may grasp to lift tray 100. A clasp 140 may be included upon or proximate to lips 120 and 122, which may be used to secure first lip 120 to second lip 122, which in turn secures base component 102 to lip component 104. Clasp 140 may also be considered a handle. Although clasp 140 is shown in the figures as being detachable from lips 120 and 122, clasp 140 may be coupled to tray 100. For example, it may be rotatably connected to lip 122 such that it may be rotated between a first configuration in which it secures lip 120 to lip 122 and a second configuration in which it does not secure lip 120 to lip 122.

Base component 102 may have a height, $H_B$, defined as the distance between first top wall 106 and first bottom wall 110. Lid component 104 may have a height, $H_L$, defined as the distance between second top wall 112 and second bottom wall 116. Accordingly, the height of internal volume 118 may be $H_B + H_L$. In some embodiments, base component 102 is shallower than lid component 104. That is $H_B$ is less than $H_L$. In some embodiments, $H_L$ is approximately 1.5 times to 10 times longer than $H_B$. For example, in some embodiments, $H_L$ may be three times longer than $H_B$.

Figure 3:
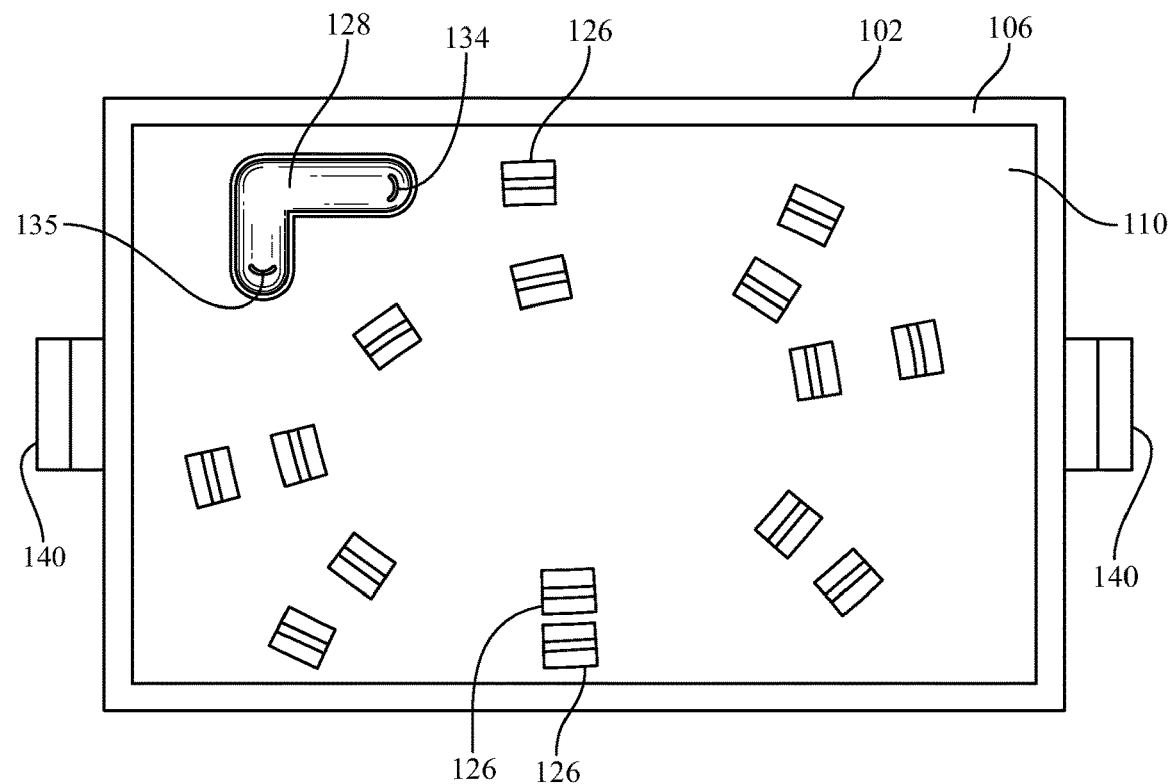
FIG. 3 depicts a top view of a base component of the sterilization tray of FIG. 1.
Figure 4:
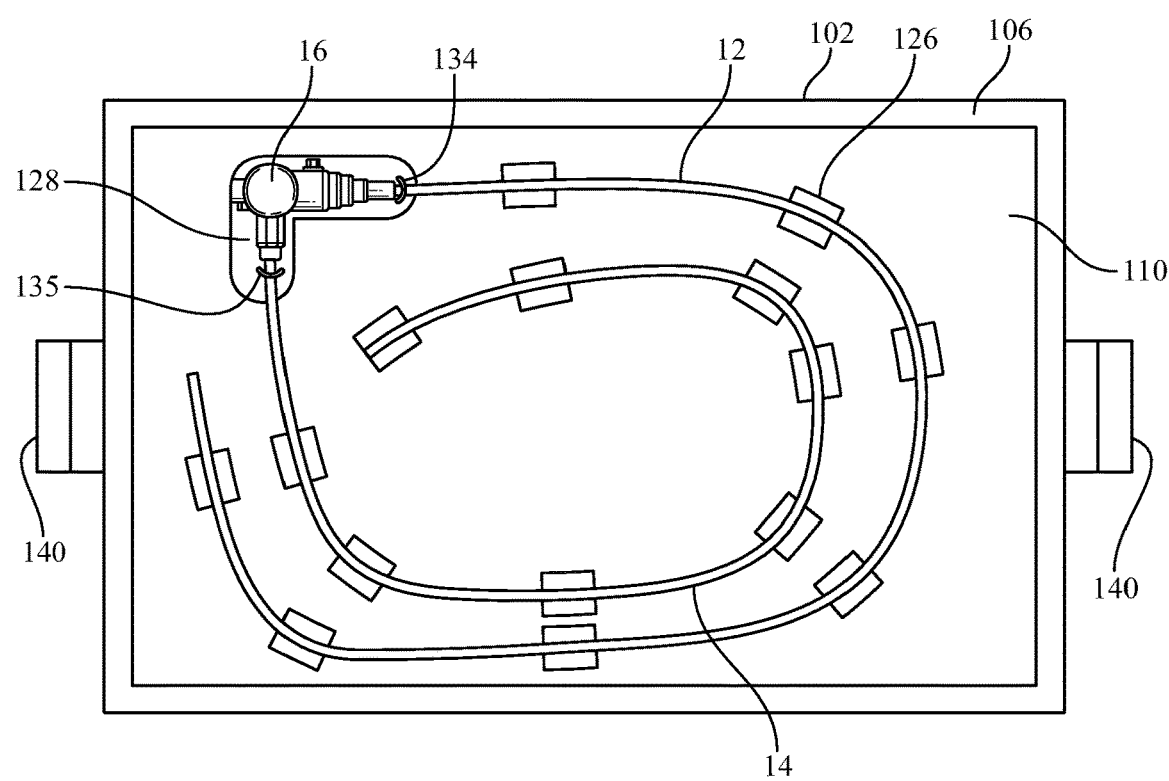
FIG. 4 depicts the top view of the base component with an endoscope disposed therein.
Figure 5:
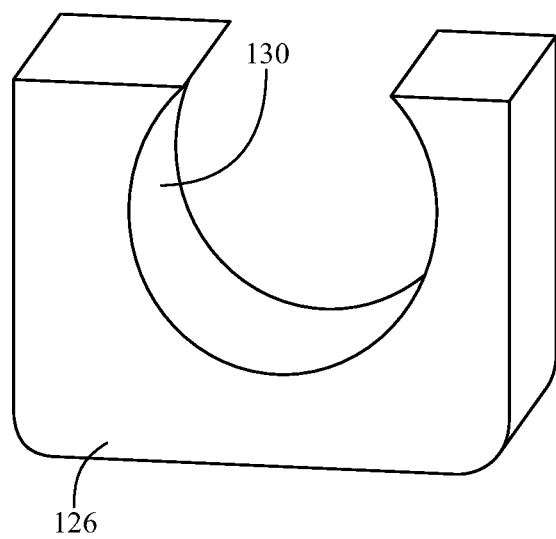
FIG. 5 depicts a bracket that may be disposed within the base component.

Referring to FIGS. 3 and 4, between one and twenty brackets, e.g., at least two brackets 126, may be disposed upon first bottom wall 110. FIG. 5 details an example of a bracket 126. Bracket 126 may have an internal profile 130 that conforms closely to an insertion tube 12 and/or umbilical tube 14 of an endoscope such that the tubes may be positioned in brackets 126 to be held in place by brackets 126. Brackets 126 may be somewhat flexible to facilitate placement of tube 12 and/or 14 therein, while still providing a secure hold. Brackets 126 may be disposed in various configurations upon first bottom wall 110 in order to maintain an endoscope in a desired configuration. For example, brackets 126 may be disposed about first bottom wall 110 in a spiral or coiled configuration such that an endoscope may be maintained by brackets 126 in a spiral or coiled configuration. An insert 128 may also be disposed upon first bottom wall 110. Insert 128 should have an internal profile that conforms closely to a body 16 of an endoscope. Insert 128 may include a securing mechanism or mechanisms, such as elastomeric bands 134 and 135, to secure body 16 to insert 128. FIG. 4 shows an endoscope within base component 102, secured by brackets 126 and bands 134, 135 in a coiled configuration.

In use, tray 100 may be used according to the following procedure. First, at a point-of care, e.g., in a procedure room, such as an operating room, lid component 104 may be positioned with second top wall 112 disposed below second bottom wall 116 such that an endoscope may be disposed within lid component 104 upon second top wall 112. Initial steps of a reprocessing procedure may be performed with the endoscope disposed within lid component 104. Second, lid component 104 may be covered by base component 102. Further, holes 132 may be covered by, e.g., a disposable plastic film to avoid potential bioburden exposure during transportation to a reprocessing area of a healthcare facility. Third, tray 100 may be transported, with the endoscope inside of it, to the reprocessing area. Fourth, base component 102 may be removed from atop lid component 104 and the base component flipped so that first bottom wall 110 is disposed below first top wall 106. Fifth, the endoscope's tubes (e.g., insertion tube 12 and umbilical tube 14) may be positioned within brackets 126, e.g., in a coiled configuration. The endoscope's body (e.g., body 16) may also be positioned within insert 128. The endoscope's body may be secured to insert 128 with band 134. Sixth, lid component 104 is disposed atop base component 102. Seventh, tray 100 is positioned in a sterilizer, e.g., the STERRAD® System, STERRAD® NX System or STERRAD® 100NX System of Advanced Sterilization Products, Division of Ethicon US, LLC, a Johnson & Johnson company. Eighth, tray 100, with the endoscope therein, is subject to a sterilization procedure. Ninth, tray 100 may be transported to a procedure room, such as an operating room. Tenth, the process may be repeated.

Accordingly, tray 100 may be considered reversible in nature. Referring to the foregoing exemplary procedure, base component 102 is disposed atop lid component 104 from the second through the fourth steps, whereas lid component 104 may be disposed atop base component 102 from the sixth through ninth steps. The reversible nature of the tray helps ease management of the endo scope and reduces the number of supplies used during a reprocessing procedure.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A sterilization tray, comprising,
    a base component having a first top wall, a first side wall, and a first bottom wall;
    at least two brackets disposed upon the first bottom wall;
    a lid component having a second top wall, a second side wall, and a second bottom wall, the lid component disposed atop the base component and covering the base component;
    wherein a first distance measured from the first top wall to the first bottom wall is less than a second distance measured from the second top wall to the second bottom wall.

2. The sterilization tray of claim 1 wherein the second distance is between approximately 1.5 times and ten times longer than the first distance.

3. The sterilization tray of claim 2 wherein the second distance is approximately three times longer than the first distance.

4. The sterilization tray of claim 2, further comprising a first hole disposed through the lid component.

5. The sterilization tray of claim 4, further comprising a second hole disposed through the base component.

6. The sterilization tray of claim 5, wherein the first hole is disposed through the second side wall.

7. The sterilization tray of claim 6, wherein the second hole is disposed through the first side wall.

8. The sterilization tray of claim 2, further comprising an insert disposed on the first bottom wall and configured to maintain a body of an endoscope.

9. The sterilization tray of claim 8, wherein the insert includes a securing mechanism.

10. The sterilization tray of claim 9, wherein the securing mechanism is an elastomeric band.

11. The sterilization tray of claim 2, wherein the brackets are configured to maintain an endoscope in a coiled configuration.

* * * * *